United States Patent [19]
deGuillebon et al.

[11] Patent Number: 5,263,958
[45] Date of Patent: Nov. 23, 1993

[54] MICROSURGICAL INSTRUMENT

[75] Inventors: Henri F. deGuillebon, Manchester-by-the-Sea, Mass.; Irving Kalikow, Delray Beach, Fla.

[73] Assignee: Microline Inc., Danvers, Mass.

[21] Appl. No.: 865,097

[22] Filed: Apr. 8, 1992

[51] Int. Cl.$^5$ ............................................. A61B 17/32
[52] U.S. Cl. ..................................... 606/174; 606/167; 606/170
[58] Field of Search .................. 128/751, 754; 604/22; 606/39, 79, 131, 132, 166, 167, 169, 170, 171, 172, 174, 175, 180; 30/244, 245, 249

[56] References Cited

U.S. PATENT DOCUMENTS

| | | | |
|---|---|---|---|
| 2,708,437 | 5/1955 | Hutchins | 128/751 |
| 3,756,242 | 9/1973 | Coss | 606/167 |
| 4,258,716 | 3/1981 | Sutherland | 606/174 |
| 4,433,687 | 2/1984 | Burke et al. | 606/174 |
| 4,499,898 | 2/1985 | Knepshield et al. | 606/172 |
| 4,589,414 | 5/1986 | Yoshida et al. | 606/79 |

Primary Examiner—C. Fred Rosenbaum
Assistant Examiner—Noelle K. Gring

[57] ABSTRACT

A microsurgical instrument especially for ocular surgery including a hub having an axis with an axial bore in the proximal end and being receivable of a piston. In the distal end the bore is receivable of a tube, the piston and the tube being coaxial with the axis of the hub. A piston with an internal axial bore is disposed in the bore of the hub and is reciprocally movable along the axis. A face is disposed at one end of the piston and is adapted to engage a driver to provide movement of the piston on the axis. A tube is disposed in the bore at the distal end of the hub and extends outwardly therefrom. A member is rotatably disposed in the tube and extends outwardly to adjacent the distal end of the tube and inwardly to adjacent to the bore in the piston. Operative parts of the microsurgical instrument are disposed on the distal ends of each of the tube and the member. The parts cooperate with each other to perform a surgical task. Two spiral pathways are formed in the distal end of the piston and a pin is attached to the proximal end of the member and fitted in the spiral pathways whereby to convert longitudinal motion to rotational motion thus enabling operation of the instrument with a minimum of finger pressure.

17 Claims, 2 Drawing Sheets

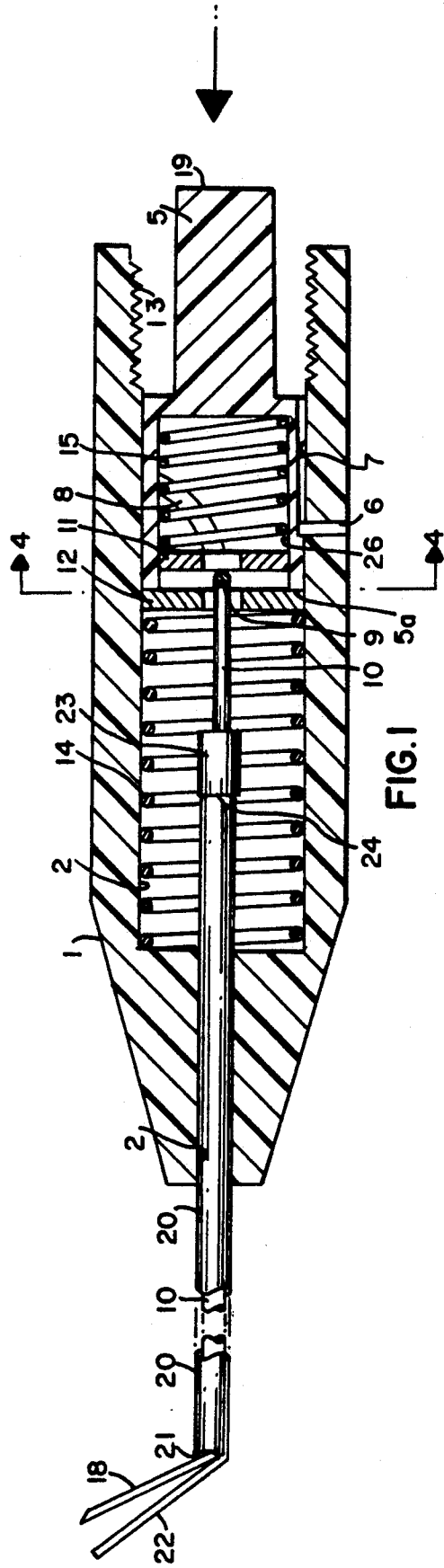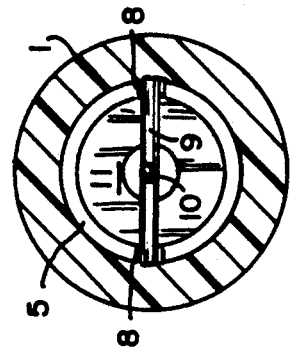
FIG. 4
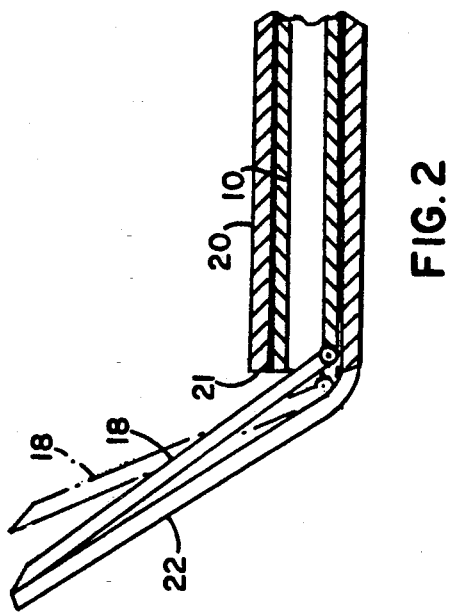
FIG. 2
FIG. 1

MICROSURGICAL INSTRUMENT

The present invention relates to improved microsurgical instruments and particularly to improved microsurgical instruments which are finger-operated with a minimum of finger pressure by a surgeon during surgery.

In microsurgery it is desirable to use instruments which are sufficiently small to enter a very small aperture, such as an incision in the eye or the body and to manipulate the instrument at various angles relative to the aperture without having to enlarge it to any extent. Moreover it is highly desirable to operate the instruments with a minimum of finger pressure and to eliminate the necessity of using lubricants within the housings of the devices.

DESCRIPTION OF THE PRIOR ART

Microsurgical scissors have previously been disclosed to cut minute segments of the retina. For example, finger-operated instruments were disclosed in which a handle is held by a surgeon and a lever is used to actuate a movable cutting blade. The U.S. Pat. No. to Sutherland, 4,258,716, discloses a hand held microsurgical instrument having a bell crank which urges against a piston to translate longitudinal motion of the piston into rotary motion of a shaft. Translation is accomplished with a spirally twisted ribbon that is fitted in a slot within the handle of the instrument. Rotation of the shaft opens and closes the movable blade of the scissors (relative to a stationary blade) since the movable blade is attached to it. The rotational movement of the movable blade against the stationary blade provides the cutting.

We have found that the movable blade should be disposed relative to the stationary blade so that the tip of the stationary blade is the most distal part of the instrument. Such disposition makes the surgery safer because unless it is so disposed the surgeon is frequently unable to know exactly where the tip of the instrument is located relative to the portion of the tissues being operated upon because the tip of the movable blade can be hidden behind the stationary blade with some of the positions it can be in.

Moreover, when employing a helical ribbon to actuate the movable blade we have found that rotational motion can be less than ideal in some situations and the blade motion can sometimes become erratic. The amount of pressure required to turn the ribbon is a significant consideration because delicate surgery necessitates delicate manipulation of the instruments. In the prior art, we have found that the torque required to open and close the instrument is quite high when using a helical ribbon in which the force has to be applied fairly close to the axis of rotation of the member being rotated. The high amount of torque that has to be applied has led to the necessity of having to lubricate the parts to reduce the torque that is necessary. Inclusion of oil in the device provides a possible source of contamination because of the possibility of leakage from the instrument.

SUMMARY OF THE INVENTION

We have found that a highly precise, easily used microsurgical instrument can be made. The instrument includes a hub with an internal axial bore disposed therein. The bore at the proximal end of the hub is adapted to receive a piston and the bore at the distal end is adapted to receive a very small diameter tube (the diameter of the bore at the distal end of the hub being significantly less then the bore at the proximal end).

The piston and the tube are coaxial with the axis of the hub.

The piston is reciprocally movable in the hub along the axis and controlled by the doctor applying finger pressure. A second bore is disposed inside of the piston and is fitted with a means to translate lateral movement to rotational movement, the means being at least one and preferably two spiral pathways disposed on the bore. A rotatable member, preferably a rod or tube, is fitted inside the fixed tube and is free to rotate therein. A pin is welded to the proximal end of the rotatable member and travels in the spiral pathways and rotates. Since the pin is attached to the rotatable member, the member rotates also. The torque required to rotate the pin (and thus the rotatable member) is low because it is applied to the distal ends of the pin as it rides in the guideway at or nearly adjacent to the axis of rotation as is the case with the prior art.

Two blades are welded to the distal ends of the tube and the rotatable member. The blade attached to the tube is the stationary blade and the blade attached to the rotatable member is the movable blade. The cutting action of the scissors is accomplished by moving the movable blade relative to the stationary blade whereby the snipping can take place. The disposition of the tip of the stationary blade at the distal end of the instrument enables the surgeon to know where the end of the blade is at all times during surgery, even as it is moved around within the surgical field, thus providing greater safety during the surgery.

Pushing the piston inwardly in the hub causes the movable blade to urge against the stationary blade and cut. Thus, longitudinal motion of the piston along the axis of the hub is translated into rotational movement with an extremely simple and dependable translation mechanism which reacts with only a minimum of pressure.

BRIEF DESCRIPTION OF THE DRAWINGS

FIG. 1 of the drawings is a cross-sectional view of the microsurgical instrument according to the present invention.

FIG. 2 is an enlarged view of the tip of the microsurgical instrument showing the movement of the movable blade relative to the stationary blade.

FIG. 4 is a cross-sectional view of the hub and the piston taken along the line 4—4 of FIG. 1.

DESCRIPTION OF THE PREFERRED EMBODIMENTS

Figure 3A:
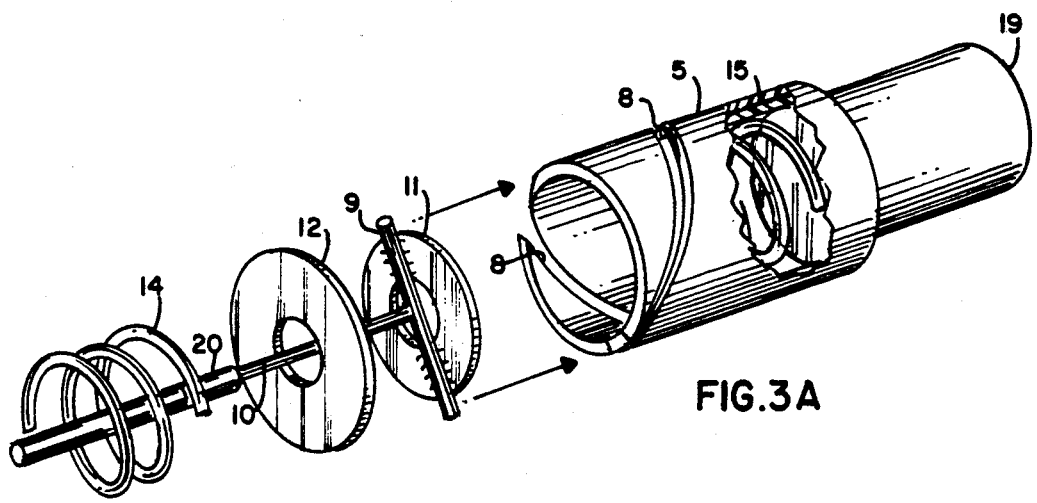
FIGS. 3A and 3B are views of the piston as shown in FIG. 1 for the translation of linear motion to rotational motion.
Figure 3B:
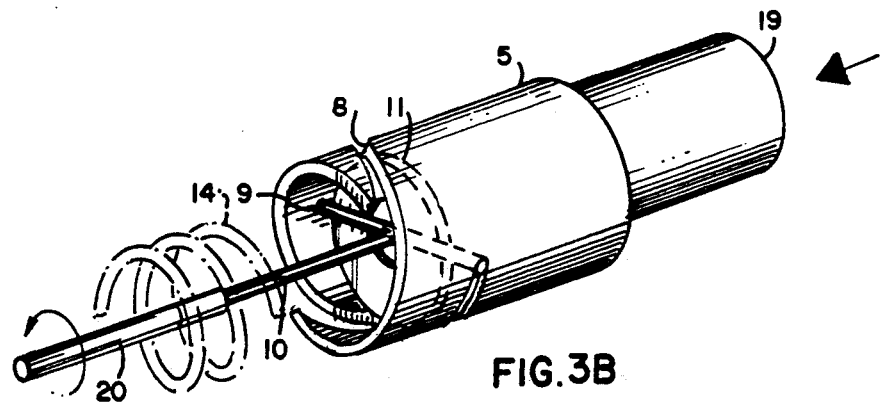

Referring now to FIG. 1, a hub 1 is shown having a cylindrical hub bore 2. The hub bore 2 has a uniform diameter and is axially disposed within the hub 1. It extends over substantially the entire length of the hub 1. The hub bore 2 terminates in internal threads 13 which are adapted to receive a suitable actuation device, any of the commonly available ones being adequate. A piston 5 is slidably disposed within the hub bore 2 and moves along the axis of the hub 1. The piston 5 is restrained both in longitudinal and rotational motion by a pin 6 which is fixedly disposed through the wall of hub 1 and extends inwardly to a guideway 7 formed in piston 5. The pin 6 prevents the piston 5 from moving past a predetermined point and also prevents rotational movement of piston 5 as the piston 5 is moving along the axis of hub 1.

A cylindrically-shaped piston bore 26 is formed within piston 5, the axis of the bore being coaxial with the axis of the hub 1. Two spiral pathways 8 are formed on the distal end of the piston bore 26 and act as part of the translation mechanism to change longitudinal movement along the axis of hub 1 to rotational movement of the microsurgical instrument which will be explained hereinafter.

The proximal end of piston 5 has a flat face 19 disposed thereon which is adapted to engage the actuation device which will move piston 5 along the axis of hub 1. A translation pin 9 is welded to the proximal end of a rid or tube 10 (herein called member) at right angles to the axis of member 10. As the distal ends of pin 9 enter spiral pathways 8 and more along it, member 10 rotates relative to hub 1. Since the ends of the pin 9 are distantly spaced from the axis of rotation and it is these ends that are turned by the spiral pathways 8 in the piston 5, the torque necessary to turn the pin 9 is considerably reduced from the situation of having a force applied immediately adjacent the axis of rotation of the member being turned.

As seen in FIG. 4, pin 9 is disposed in the spiral pathways 8. As spiral pathways 8 advance by pushing piston 5, translation pin 9 will rotate thereby rotating member 10 that is attached to it. As piston 5 is urged inwardly toward the distal end of hub 1 and sliding within hub bore 2 the proximal end 5a urges against a washer 12 which rides within hub bore 2. Washer 12 is urged toward the proximal end of hub 1 by means of a spring 14 which exerts a pressure between the interior of hub bore 2 and washer 12 to enable washer 12 to return to a predetermined point when the pressure is removed from the flat face 19 of piston 5. In order to ensure that pin 9 (and member 10 which is carried by pin 9) returns to a predetermined point within hub 1 to insure the proper redisposition of the instrument parts, a spring 15 is disposed within piston bore 26 and urges against washer 11.

Thus, the rotation of pin 9 and member 10 which is welded to it and washer 11 is provided by urging flat face 19 of piston 5 toward the distal end of hub 1 to provide for translating this longitudinal motion into rotational movement of member 10. The rotational movement is maintained on the axis of hub 1 by means of washers 11 and 12 and the return to a predetermined position is ensured by springs 14 and 15. The movement in the spiral pathways 8 enables the member 10 to be disposed in a predetermined location whereby the movement of member 10 is controlled.

In the embodiment disclosed the instrument which is being operated is a scissor. Scissors, in this case, have a movable blade 18 and a stationary blade 22. The movable blade 18 is affixed to member 10 and will rotate, within limits, when member 10 is rotated. Stationary blade 22 is disposed at the end of a tube 20 in which is disposed member 10.

As shown in FIG. 2, stationary blade 22 is attached to member 20, which in this case is another tube of slightly larger diameter. A recess 21 is cut at the end of tube 20 to enable movable blade 18 to rotate and engage stationary blade 22. In the preferred embodiment for ocular surgery the blades are welded to the ends of two concentric tubes, each having lengths sufficient to allow entry from the side of the eye to reach the retina and movably explore the vitreous portion of the eye. Preferably the tubes extend from the distal end of the hub 1 by about 1 to 1.5 inches. The cutting blades are attached to the tubes by welding at an angle of 55° to allow cutting action close to the retina. The actual cutting is conducted by the stationary blade 22 at the extreme distal end of the tube 20. The entire movable blade 18 is always visible to the surgeon through an optical microscope which is used during the surgery. Such visibility is preferred over existent cutting devices in which the tip of a movable blade is outside of the stationary blade. We have found that when the movable blade is hidden from view and is close to the retina that operation of the device is more difficult and dangerous.

Control stop 23 is provided to insure that movable blade 18 is positioned to properly engage fixed blade 22 for optimal cutting and also to prevent excess pressure from damaging the delicate cutting blades 18 and 22. Control stop 23 is welded to inner tube 10 and face 24 rotates against and is positioned by the proximal end of tube 20.

It is apparent that modifications and changes can be made within the spirit and scope of the present invention. It is our intention, however, only to be limited by the scope of the appended claims.

As our invention we claim

1. A surgical instrument comprising:

a hub having distal and proximal ends;

a hub bore disposed on the axis of said hub;

a tube disposed in said hub bore at the distal end of said hub and extending outwardly therefrom, said tube being disposed on the axis of said hub;

a piston having distal and proximal ends disposed in said hub bore at the proximal end of said hub, said piston being disposed coaxially with said tube, said piston being reciprocally movable in said hub bore on said axis, said piston having a face at its proximal end, said face being adapted to engage a driver to provide movement of said piston on said axis;

a piston bore disposed in said piston at its distal end;

a member having distal and proximal ends rotatably disposed in said tube, the proximal end of said member being disposed adjacent the distal end of said piston;

a surgical device disposed on the distal ends of each of said tube and said member, said surgical device being formed of more than one part, said parts cooperating with each other to perform a surgical task;

translation means on said piston operatively associated with a rotational means to change lateral motion of said piston on said axis to rotational motion of said member with a minimum of torque, said translation means including at least one spiral pathway formed in the piston bore, said rotational means being disposed on the proximal end of said member and including a translation pin disposed normal to said member, said translation pin being arranged to travel in said spiral pathway;

means to prevent rotation of said piston about said axis during said lateral motion;

a first spring and a first washer disposed within said hub bore, the distal end of said piston being arranged in forward travel to urge against said washer to compress the spring and rotate said member and further to provide (in return travel) for counter rotation of said member; and a second spring and a second washer disposed within said piston bore, said translation pin engaging said second washer in forward travel to urge against said second washer and compress said second spring to provide in return travel for counter rotation of said member.

2. The surgical instrument according to claim 1 wherein there are two spiral pathways and the pin has two ends, each end engaging one of the pathways.

3. A surgical instrument comprising:
a hub having an axis and distal and proximal ends;
an axial hub bore disposed in said hub, the proximal end of said hub bore containing a piston and a distal end containing a tube, said piston and said tube being disposed coaxially with the axis of said hub, said tube being disposed in said hub bore at the distal end thereof and extending outwardly therefrom;
said piston having distal and proximal ends, said piston being reciprocally movable in said hub bore on said axis, said piston having a face at its proximal end, said face being adapted to engage a driver to provide movement of said piston on said axis, said piston further having an axial piston bore disposed therein at its distal end;
a member rotatably disposed in said tube, said member extending outwardly at its distal end from said tube and inwardly at its proximal end to adjacent the distal end of said piston;
a surgical device disposed on the distal ends of each of said tube and said member, said surgical device being formed of more than one part, said parts cooperating with each other to perform a surgical task;
rotational means on said member to rotate said member relative to said tube, said means being disposed within the hub bore on the proximal end of said member;
translating means in said piston bore operatively associated with the rotational means whereby to change lateral motion of said piston on said axis to rotational motion of said member with a minimum of torque;
means to prevent rotation of said piston about said axis during said lateral motion.

4. The surgical instrument according to claim 1 wherein said translation means is at least one spiral pathway formed in the bore of said piston and the means to rotate said member is a pin disposed normal to said member and attached to the proximal end thereof, said pin being arranged to travel in said spiral pathway.

5. The surgical instrument according to claim 2 wherein there are two spiral pathways and the pin has two ends, each end engaging one of the pathways.

6. The surgical instrument according to claim 3 further including a spring and a washer disposed within said hub bore, the distal end of said piston being arranged in forward motion to urge against said washer to compress the spring and rotate said member and further to provide (in return motion) for counter rotation of said member.

7. The surgical instrument according to claim 1 wherein the surgical means is a pair of scissors, one of the scissors being attached to said tube and the other of said scissors being attached to said member.

8. The surgical instrument according to claim 6 wherein the means to prevent rotation of the piston is a slot disposed in said piston cooperatively associated with a pin disposed in the hub.

9. The surgical instrument according to claim 7 further including a stop fixedly attached to said member whereby to prevent excessive pressure on said piston from damaging said surgical instrument.

10. A microsurgical instrument comprising:
a hub having an axis, an axial hub bore disposed therein and proximal and distal ends, the hub bore containing a piston in the proximal end and containing a tube in the distal end;
said piston having distal and proximal ends said piston being reciprocally movable in said hub bore on said axis, said piston having a face at its proximal end, said face being adapted to engage a driver to provide movement of said piston on said axis, said piston further having an axial piston bore disposed therein extending from its distal end;
said tube extending outwardly from said hub, said tube and said piston being disposed coaxially with the axis of said hub bore;
a member rotatably dispose din said tube, said member extending outwardly to adjacent the distal end of said tube and inwardly to adjacent the piston bore;
a microsurgical instrument diposed on the distal ends of each of said tube and said member, said microsurgical instrument being formed of more than one part, said parts cooperating with each other to perform a surgical task;
a translation pin disposed on the proximal end of said member normal to said member; and
a spiral pathway disposed in said piston bore, said spiral pathway being operatively associated with said translation pin whereby to change lateral motion of said piston on said axis to rotational motion of said member on said axis.

11. The microsurgical instrument according to claim 10 further including a spring and a washer disposed within said hub bore, the distal end of said piston being arranged in its forward motion to urge against said washer to compress said spring and rotate said member and to provide in return motion for counter rotation of said member.

12. The microsurgical instrument according to claim 10 wherein the surgical means is a pair of scissors, one of the scissors being attached to said tube and the other of said scissors being attached to said member.

13. The microsurgical instrument according to claim 10 further including means to prevent rotation of said piston around said axis.

14. The microsurgical instrument according to claim 13 wherein the means to prevent rotation of the piston is a slot disposed on the outer wall of said piston cooperatively associated with a rotational pin disposed in the hub.

15. The microsurgical instrument according to claim 10 wherein the tip of the stationary blade is the distal most point of the instrument.

16. The microsurgical instrument according to claim 10 further including a stop fixedly attached to said member whereby to prevent excessive pressure on said piston from damaging said surgical device.

17. The microsurgical instrument according to claim 10 further including a second spring and a second washer disposed within said piston bore, said translation pin engaging said second washer in forward travel to urge against said second washer and compress said second spring to provide in return travel for counter rotation of said member.

* * * * *